United States Patent [19]
Montgomery

[11] Patent Number: 5,168,866
[45] Date of Patent: Dec. 8, 1992

[54] VAPORIZERS USABLE WITH ANESTHETICS HAVING A BOILING POINT NEAR THE AMBIENT TEMPERATURE

[75] Inventor: Frederick J. Montgomery, Bradford, England

[73] Assignee: The BOC Group plc, Surrey, England

[21] Appl. No.: 638,862

[22] Filed: Jan. 8, 1991

[30] Foreign Application Priority Data

Jan. 9, 1990 [GB] United Kingdom ............... 90000420

[51] Int. Cl.⁵ ............................................ A61M 16/00
[52] U.S. Cl. ........................... 128/203.12; 128/203.26; 128/203.27; 128/204.14; 128/204.15; 128/204.17
[58] Field of Search ........................ 128/203.12, 203.26, 128/203.27, 204.14, 204.17, 203.17, 909, 204.15

[56] References Cited

U.S. PATENT DOCUMENTS

| | | | |
|---|---|---|---|
| 2,046,633 | 7/1936 | Johnson | 128/204.14 |
| 4,572,208 | 2/1986 | Cutler | 128/718 |
| 4,587,966 | 5/1986 | Albarda | 128/202.22 |
| 4,722,334 | 2/1988 | Blackmer | 128/203.16 |
| 4,770,168 | 9/1988 | Rusz | 128/203.12 |
| 4,879,997 | 11/1989 | Bickford | 128/203.26 |
| 4,881,541 | 11/1989 | Eger et al. | 128/203.25 |
| 4,951,659 | 8/1990 | Weiler | 128/200.18 |
| 4,955,372 | 9/1990 | Blackmer | 128/203.16 |

FOREIGN PATENT DOCUMENTS

| | | | |
|---|---|---|---|
| 339828 | 11/1989 | European Pat. Off. . | |
| 1589569 | 5/1970 | France | 128/203.25 |
| 1221373 | 2/1971 | United Kingdom . | |
| 1224478 | 3/1971 | United Kingdom . | |
| 2097272 | 11/1982 | United Kingdom . | |
| 2148127 | 12/1985 | United Kingdom | 128/203.17 |
| 2190000 | 11/1987 | United Kingdom | 128/203.17 |

Primary Examiner—Edgar S. Burr
Assistant Examiner—Eric P. Raciti
Attorney, Agent, or Firm—Roger M. Rathbun; Larry R. Cassett

[57] ABSTRACT

An anesthetic vaporizer 1 of the by-pass type includes a vaporizing chamber 12 containing an anesthetic agent which at normal atmospheric pressure has a boiling point of approximately 25° C. The vaporizing chamber 12 is surrounded by thermal insulation 18 to prevent uncontrolled boiling of the anesthetic agent.

5 Claims, 2 Drawing Sheets

VAPORIZERS USABLE WITH ANESTHETICS HAVING A BOILING POINT NEAR THE AMBIENT TEMPERATURE

BACKGROUND OF THE INVENTION

The present invention relates to anesthetic vaporizers. UK Patent No 1 224 478, describes an anesthetic vaporizer of the by-pass type in which a carrier gas such as oxygen, air or nitrous oxide is initially divided on entry to the vaporizer between a first stream which is directed towards the sump or vaporizing chamber of the vaporizer to entrain vapor from a volatile liquid anesthetic contained therein; and a second by-pass stream, the first and second streams subsequently re-combining prior to leaving the vaporizer for delivery to a patient.

This known vaporizer has been used successfully over a number of years for delivering anesthetic agents such as halothane, trichloroethlne and halogenated ethers including enflurane, fluoroxene, methoxyflurane and isoflurane. All the aforementioned anesthetic agents have a boiling point at atmospheric pressure well above 40° C.

However, a new anesthetic agent has been developed namely 2-(difluoromethoxy)-1,1,1,2-tetrafluoroethane which has a boiling point at atmospheric pressure of between 20° and 25° C. This physical characteristic of 2-(difluoromethoxy)-1,1,1,2-tetrafluoroethane renders existing anesthetic vaporizers unsuitable for delivering said agent to a patient.

Conventional vaporizers of the by-pass type are unsuitable for this new anesthetic agent in that its boiling point is approximately in the middle of their operating ambient temperature range, i.e. between 15° C. and 35° C. When the ambient temperature and hence the vaporizer temperature is above 25° C., heat is transferred to the anesthetic agent which causes an amount of vapor to boil off such that heat lost by the latent heat of vaporization is equal to the heat transferred to it.

In conventional vaporizers the heat transfer to the anesthetic agent in the vaporizing chamber can be high because of the materials used and this can cause a high volume of anesthetic agent to boil off. This anesthetic vapor can leave the vaporizer via either the control valve, the by-pass valve or both.

OBJECT OF THE INVENTION

It is the object of the present invention to provide an anesthetic vaporizer which is capable of delivering to a patient a predetermined concentration of an anesthetic agent whose boiling point at normal atmospheric pressure is less than 30° C.

SUMMARY OF THE INVENTION

According to the present invention, an anesthetic vaporizer of the by-pass type comprises an inlet for carrier gas, an outlet for carrier gas and anesthetic agent, a first by-pass passage extending between the inlet and the outlet, a flow restrictor located in said first passage, a passageway extending between the inlet and the outlet having located therein a thermally insulated vaporizing chamber and a control valve, and a temperature controller located within said insulated vaporizing chamber.

BRIEF DESCRIPTION OF THE DRAWINGS

Embodiments of the invention will now be described, by way of example, reference being made to the Figures of the accompanying diagrammatic drawings in which.

DETAILED DESCRIPTION OF THE INVENTION

Figure 1:
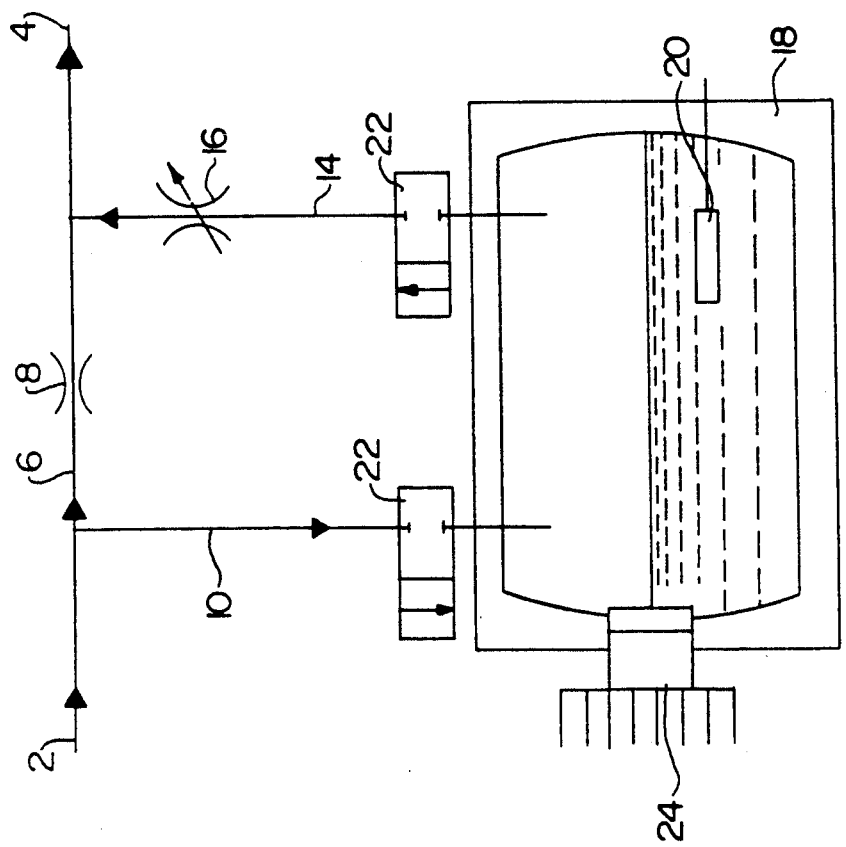
FIG. 1 is a diagrammatic sketch of a first anesthetic vaporizer.

Referring to FIG. 1, an anesthetic vaporizer 1 of the by-pass type includes a carrier gas inlet 2 and a gas and vapor outlet 4. A by-pass passage 6 containing a laminar flow restrictor 8 interconnects said inlet 2 and outlet 4. The flow restrictor 8 exhibits laminar flow characteristics over its full operating range.

A passage 10 extends from by-pass passage 6 to the interior of a vaporizing chamber 12 containing an anesthetic agent, such as 2-(difluoromethoxy)-1,1,1,2,-tetrafluoroethane which has a boiling point of 30° C. or less at normal atmospheric pressure. A passage 14 extends from the interior of the vaporizing chamber 12 back to the by-pass passage 6. Located in said passage 14 is a laminar control valve 16 which exhibits laminar flow characteristics over its full operating range.

The passages 10 and 14, together with the vaporizing chamber and the control valve 16, define a passageway between the inlet 2 and the outlet 4.

The vaporizing chamber 12 is substantially surrounded by thermal insulation material 18 which can be on the order of 20 millimeters thick to prevent or inhibit uncontrolled boiling. Located within the vaporizer 1 is a temperature controlled heater 20.

Arranged in each of passages 10, 14 is an isolator 22.

In use, the control valve 16 is set in a conventional manner to split the flow of carrier gas entering inlet 2 between a first stream which is directed along passage 10 to the interior of the vaporizing chamber 12 and a second by-pass stream which flows directly along passage 6 to the outlet 4.

The first stream enters the vaporizing chamber 12 and entrains vapor of the anesthetic agent contained therein and the carrier gas and vapor mixture leaves the vaporizing chamber 12 via passage 14 to rejoin the second stream in the by-pass passage 6 prior to leaving the anesthetic vaporizer 1 at the outlet 4.

The above described vaporizer is of the by-pass type and has a thermally insulated vaporizing chamber 12. The insulating material 18 limits the heat transfer into the vaporizing chamber 12 when the outside ambient temperature is greater than the vaporizer's designed operating temperature which is below the boiling point of the anesthetic agent.

When in use, the anesthetic agent is vaporized and the heat removed from the vaporizing chamber is equivalent to the latent heat of vaporization.

If the amount lost via latent heat of vaporization is greater than the heat transfer coming from the outside then the temperature in the vaporizing chamber 12 will fall.

The temperature controlled heater 20 prevents the temperature in the vaporizing chamber 12 falling below a set value and provides the heat required to evaporate the anesthetic agent needed for the carrier gas flow and high concentration settings of the vaporizer 1.

The amount of insulating material 18 is specified to ensure that the heat lost through latent heat of vaporization is always greater than that gained from heat transfer through the vaporizing chamber walls over the required range of carrier gas flow rates and concentration settings.

When the anesthetic agent is 2-(difluoromethoxy)-1,1,1,2,-tetrafluoroethane, utilizing a minimum flow and concentration are specified as one liter per minute and 1% concentration by volume of agent, respectively, the latent heat loss from vaporization would be approximately 0.17 watts. If the operating temperature of the vaporizing chamber 12 is designed to be 22° C. and the maximum ambient temperature for operating the vaporizer 1 is 30° C. then a typical thickness of expanded polystyrene insulating material 18 would need to be on the order of 20 mm.

If the vaporizer control valve 16 is left in an on position, there is no carrier gas flow and the ambient temperature is above the boiling point of the anesthetic agent, an amount of vapor equivalent to the heat transferred to the vaporizing chamber 12 will boil off. Over a period of time, this would result in filling the gas circuits of the anesthetic apparatus with anesthetic vapor. This could give a dangerous concentration to a patient if connected to the circuit and the carrier gas were to be turned on.

To prevent this situation, the isolators 22 can be actuated to isolate the vaporizing chamber from the rest of the vaporizer when there is no carrier gas flow. When the vaporizer 1 is in the off position, the vaporizing chamber 12 can be isolated by the control valve 16. However, heat transfer to the vaporizing chamber 12 can still occur if there is a high ambient temperature. There are number of ways to accommodate this situation.

First, when in the off position, the vaporizing chamber 12 could be vented to the atmosphere. An amount of anesthetic vapor equivalent to the heat transfer would boil off nd be wasted, but the temperature and pressure in the vaporizing chamber 12 would remain at the boiling point of the anesthetic agent, about 22° C. and ambient pressure, respectively. When turned on, the vaporizer 1 would operate normally almost immediately with little deviation from the set concentration.

Second, the vaporizing chamber 12 could be isolated when the control valve 16 is in the off position. In this case, the temperature in the vaporizing chamber 12 will slowly rise to ambient temperature and the pressure will rise above ambient pressure in line with the anesthetic agent's saturated vapor pressure characteristics. When turned on, the vaporizer 1 would boil off vapor until the temperature and pressure in the vaporizing chamber 12 return to normal level.

This could result in an initially high concentration of anesthetic being delivered to the patient. However, this initial bolus of vapor could be vented off to the atmosphere before connecting the vaporizing chamber 12 to the rest of the vaporizer gas passages.

Figure 2:
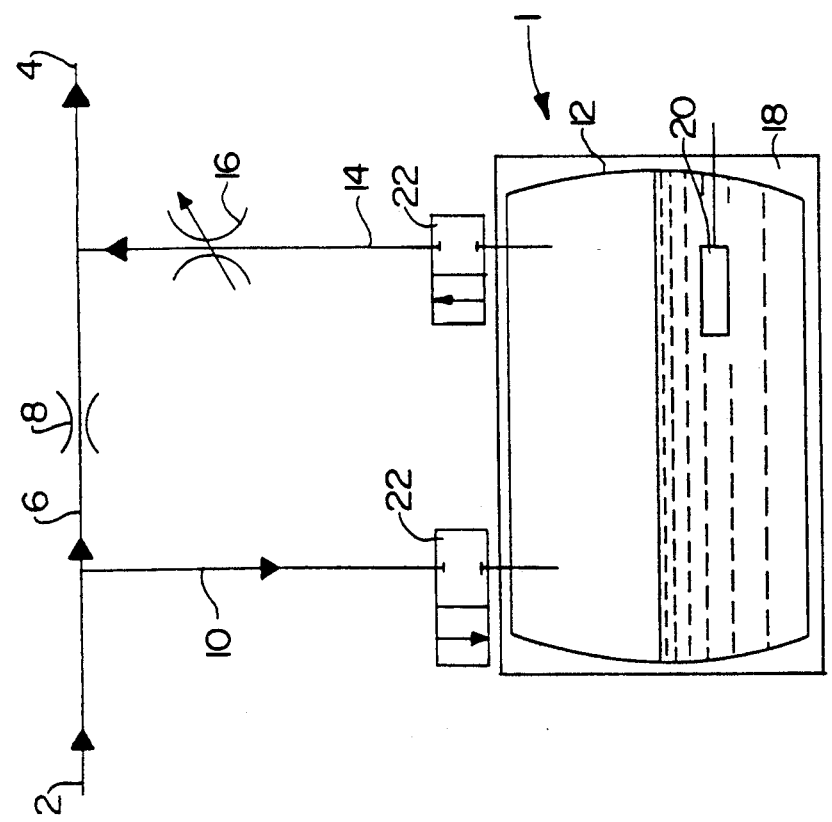
FIG. 2 is a diagrammatic sketch of a modified anesthetic vaporizer.
Figure 3:
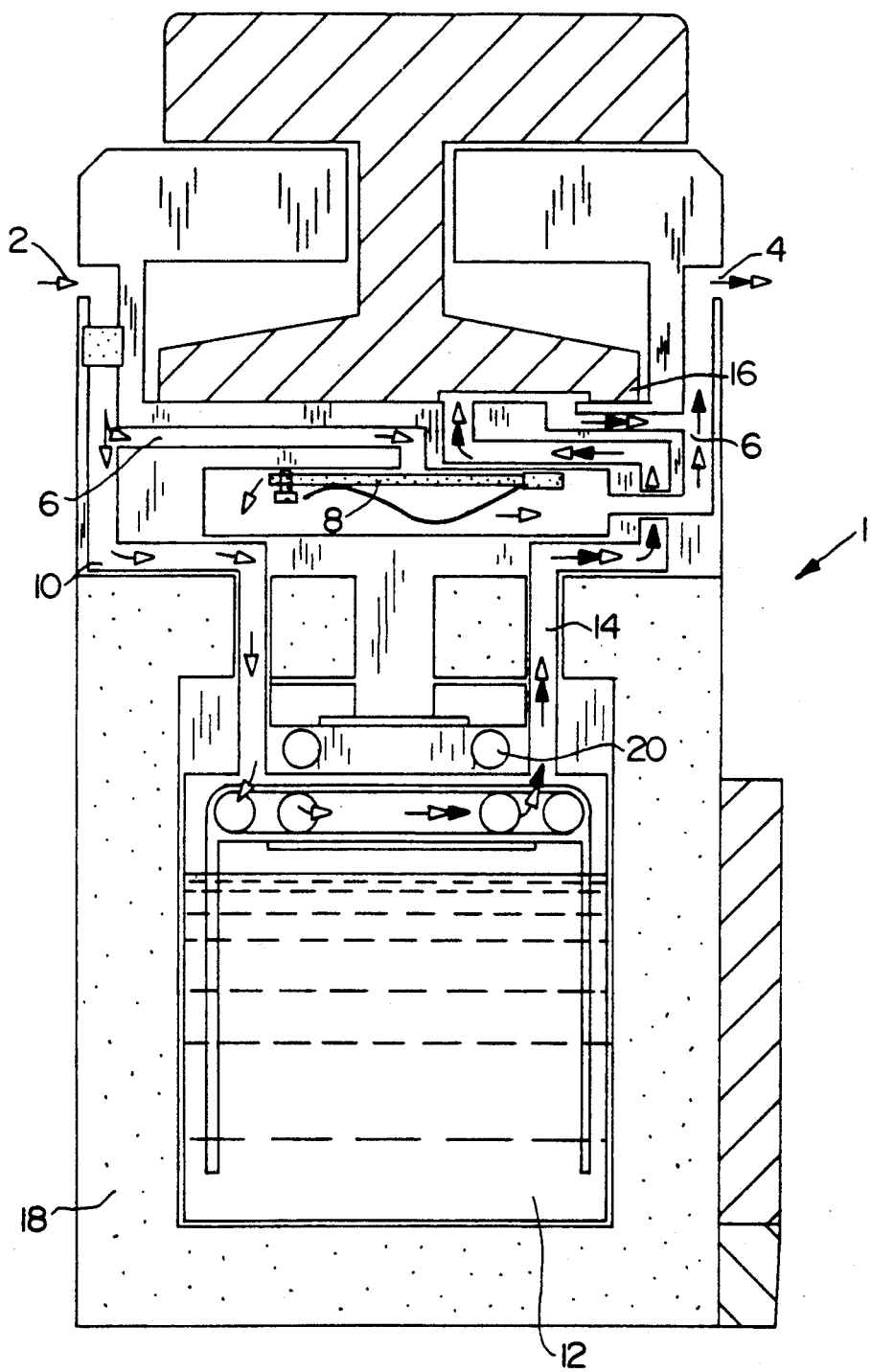
FIG. 3 is a side view partly in cross-section of the anesthetic vaporizer of FIG. 2.

Third, and with reference to FIGS. 2 and 3 where like reference numerals denote like features, the heater 20 of FIG. 1 can be supplemented by or replaced by a Peltier device 24 which, when supplied with a suitable electric current, can cool or heat the anesthetic agent contained within the vaporizing chamber 12.

Hence, the vaporizing chamber 12 can be isolated as above but rather than venting off the anesthetic when the vaporizer 1 is turned on, the Peltier device 24 can be used to cool the vaporizing chamber 12 down to its operating temperature before it is opened and the vaporizer is operational.

In this circumstance, the requirement for thermal insulation would be less than with the other embodiment as the Peltier device 24 could keep the vaporizing chamber 12 cool instead of relying totally on anesthetic vaporization.

I claim:

1. An anesthetic vaporiser of the by-pass type comprising:
   (a) an inlet for delivery of carrier gas into the vaporiser,
   (b) an outlet for delivery of carrier gas and anesthetic agent from the vaporiser to a patient,
   (c) a by-pass passage extending between the inlet and the outlet, and a flow restrictor located in the by-pass passage,
   (d) a passageway extending between the inlet and the outlet, the passageway containing (i) a thermally insulated vaporising chamber and (ii) a control valve, and
   (e) a temperature controlling device, located within the insulated vaporising chamber, which includes an element for cooling anesthetic agent located within the chamber when the vaporiser is in use, and an element for heating the said anesthetic agent.

2. An anaesthetic vaporizer as claimed in claim 1, in which the elements for heating the anaesthetic agent and cooling the anaesthetic agent respectively are provided by a single element.

3. An anaesthetic vaporizer as claimed in claim 1, in which the temperature controlling device includes a temperature controlling Peltier device.

4. An anesthetic vaporiser as claimed in claim 3, in which the temperature controlling device includes a supplementary heater for the anesthetic agent, in addition to the said element for heating.

5. An anaesthetic vaporizer as claimed in claim 1, which includes isolators located in the said passageway by which flow of carrier gas to, and flow of carrier gas and anaesthetic agent from, the vaporizing chamber is preventable.

* * * * *